United States Patent
Nguyen et al.

(10) Patent No.: US 9,334,516 B2
(45) Date of Patent: May 10, 2016

(54) METHOD FOR ADDING ENZYMES TO OBTAIN HIGH ETHANOL YIELD FROM CEREAL MASH

(71) Applicant: Abengoa Bioenergy New Technologies, LLC, Chesterfield, MO (US)

(72) Inventors: Quang A. Nguyen, Chesterfield, MO (US); Carlos Maria Retortillo Perez, Ellisville, MO (US)

(73) Assignee: Abengoa Bioenergy New Technologies, Inc., Chesterfield, MO (US)

( * ) Notice: Subject to any disclaimer, the term of this patent is extended or adjusted under 35 U.S.C. 154(b) by 82 days.

(21) Appl. No.: 14/208,057

(22) Filed: Mar. 13, 2014

(65) Prior Publication Data

US 2014/0315270 A1 Oct. 23, 2014

Related U.S. Application Data

(60) Provisional application No. 61/781,661, filed on Mar. 14, 2013.

(51) Int. Cl.
| C12P 7/14 | (2006.01) |
| C12P 19/14 | (2006.01) |
| C12P 7/10 | (2006.01) |
| C12P 19/02 | (2006.01) |

(52) U.S. Cl.
CPC . *C12P 19/14* (2013.01); *C12P 7/10* (2013.01); *C12P 19/02* (2013.01); *C12Y 302/01001* (2013.01); *Y02E 50/17* (2013.01); *Y02P 20/52* (2015.11)

(58) Field of Classification Search
CPC ............ C12P 19/14; C12P 19/02; C12P 7/10; Y02E 50/17; C12Y 302/01001
See application file for complete search history.

(56) References Cited

U.S. PATENT DOCUMENTS

| 4,490,469 | A | 12/1984 | Kirby et al. |
| 5,231,017 | A | 7/1993 | Lantero et al. |
| 7,452,425 | B1 | 11/2008 | Langhauser |
| 7,488,390 | B2 | 2/2009 | Langhauser |
| 7,662,617 | B2 | 2/2010 | Rush |
| 7,820,418 | B2 | 10/2010 | Karl et al. |
| 7,919,291 | B2 | 4/2011 | Lewis et al. |
| 8,119,384 | B2 | 2/2012 | Viksoe-Nielsen et al. |
| 8,304,212 | B2 | 11/2012 | Baez-Vasquez et al. |
| 2006/0246558 | A1 | 11/2006 | Jakel et al. |
| 2007/0037267 | A1 | 2/2007 | Lewis et al. |
| 2007/0202583 | A1 | 8/2007 | Smith et al. |
| 2008/0286845 | A1 | 11/2008 | Olsen |
| 2008/0305206 | A1 | 12/2008 | Bisgaard-Frantzen et al. |
| 2008/0318284 | A1 | 12/2008 | Soong et al. |
| 2009/0017511 | A1 | 1/2009 | Olsen et al. |
| 2009/0117630 | A1 | 5/2009 | Olsen et al. |
| 2009/0117633 | A1 | 5/2009 | Bradley et al. |
| 2009/0221041 | A1 | 9/2009 | Aux |
| 2009/0258106 | A1 | 10/2009 | Jansen et al. |
| 2009/0305935 | A1 | 12/2009 | Cascao-Pereira et al. |
| 2010/0000946 | A1 | 1/2010 | Hughes et al. |
| 2010/0196537 | A1 | 8/2010 | Konieczny-Janda et al. |
| 2010/0233319 | A1 | 9/2010 | Yamamoto |
| 2010/0260889 | A1 | 10/2010 | Elvig |
| 2011/0183395 | A1 | 7/2011 | Allain et al. |
| 2011/0223639 | A1 | 9/2011 | Lantero et al. |
| 2012/0045545 | A1 | 2/2012 | Mielgo et al. |
| 2012/0107920 | A1 | 5/2012 | Taneda et al. |
| 2012/0129234 | A1 | 5/2012 | McDonald et al. |
| 2012/0244591 | A1 | 9/2012 | Brotherson |

FOREIGN PATENT DOCUMENTS

| EP | 2164975 B1 | 7/2008 | | |
| WO | 9713841 | 4/1997 | | |
| WO | 2005005646 | 1/2005 | | |
| WO | 2005079193 | 9/2005 | | |
| WO | 2005087937 | 9/2005 | | |
| WO | WO 2006004748 A2 * | 1/2006 | ................ | C12P 7/06 |
| WO | 2006048503 | 5/2006 | | |
| WO | 2006086792 | 8/2006 | | |
| WO | 2006104504 | 10/2006 | | |
| WO | 2008023060 | 2/2008 | | |
| WO | 2011056991 | 5/2011 | | |
| WO | 2011100073 | 8/2011 | | |
| WO | 2011140222 | 11/2011 | | |
| WO | 2012099967 | 7/2012 | | |
| WO | 2012112241 | 8/2012 | | |
| WO | 2013170034 | 11/2013 | | |

OTHER PUBLICATIONS

Kumar P. et al., "Methods for Pretreatment of Lignocellulosic Biomass for Efficient Hydrolysis and Biofuel Production", Ind. Eng. Chem. Res., Online published on Mar. 20, 2009, pp. A-Q (downloaded from http://pubs.acs.org on Mar. 26, 2009).*

Erdei B., et al., Ethanol production from mixtures of wheat straw and wheat meal, Biotechnology for Biofuels, 3(16) (2010).

Tucker, M., et al., "Conversion of Distiller's Grain into Fuel Alcohol and a Higher-Value Animal Feed by Dilute-Acid Pretreatment", Applied Biochemistry and Technology, vol. 113-166, pp. 1139-1160 (2004).

International Search Report and Written Opinion for PCT/US2014/025468 dated Jun. 30, 2014; 9 pages.

* cited by examiner

*Primary Examiner* — Satyendra K Singh

(74) *Attorney, Agent, or Firm* — Armstrong Teasdale LLP

(57) ABSTRACT

The present invention generally relates to processes for production of monosaccharides and ethanol from energy crops. In some aspects, the present invention relates to improvements in ethanol production from energy crops including fractionating liquefied mash to generate a fraction enriched in complex polysaccharides such as cellulose, conversion of the cellulosic components to monosaccharides, and preparation of ethanol therefrom.

23 Claims, 1 Drawing Sheet

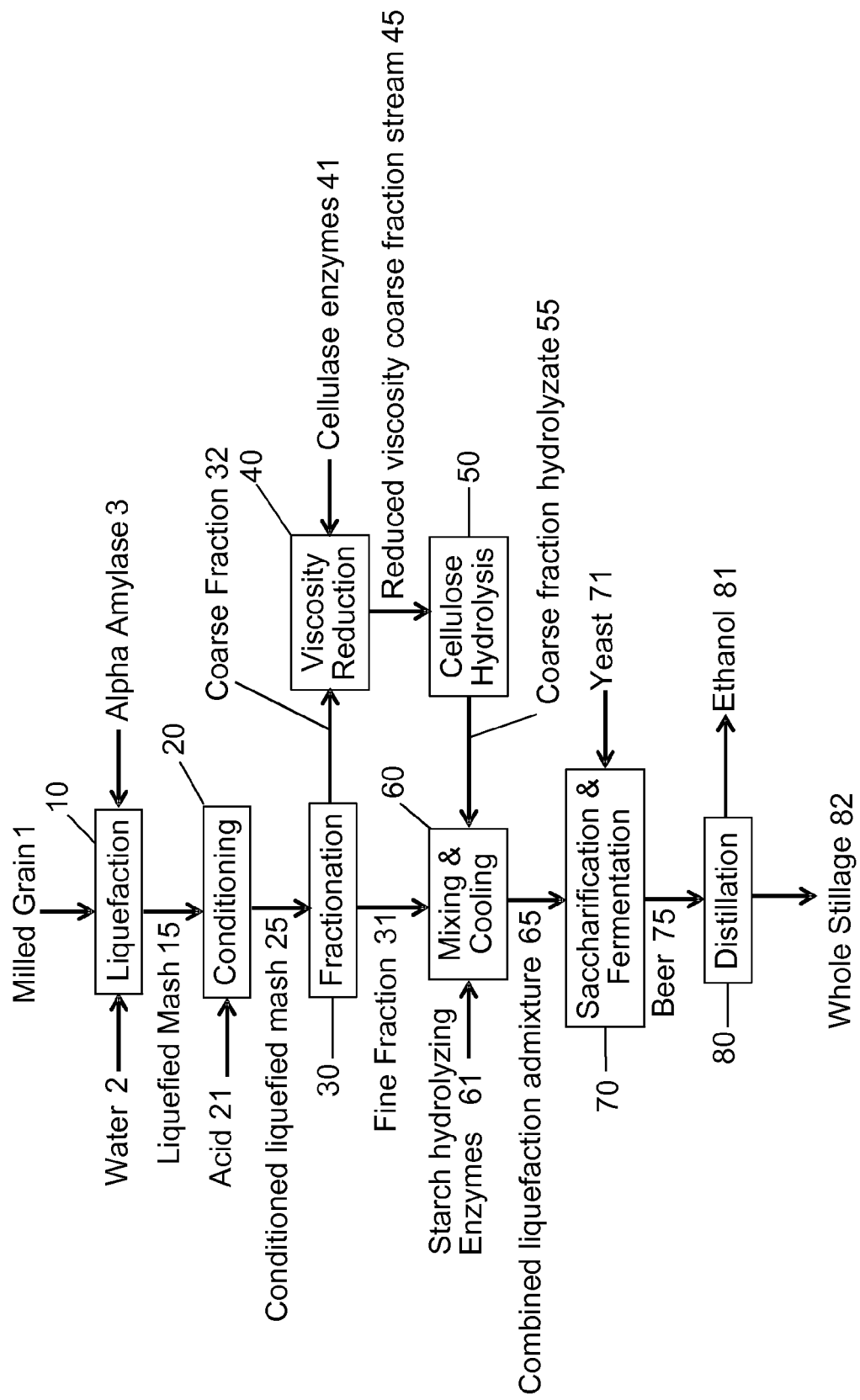

METHOD FOR ADDING ENZYMES TO OBTAIN HIGH ETHANOL YIELD FROM CEREAL MASH

CROSS REFERENCE TO RELATED APPLICATIONS

This application claims the priority of U.S. Provisional Patent Application Ser. No. 61/781,661, filed Mar. 14, 2013, which is hereby incorporated by reference in its entirety.

BACKGROUND OF THE INVENTION

The present invention generally relates to processes for production of ethanol from energy crops. The present invention further relates to improvements in one or more aspects of ethanol production from energy crops including, for example, improved methods for fractionating liquefied mash, improved efficiency of conversion of energy crop cellulosic components to monosaccharides, and improved yield of ethanol from energy crops.

Ethanol and corresponding co-products may be produced from a variety of starch-containing energy crops, such as grain and tubers, using any conventional dry mill or wet mill fermentation process known in the art. For example, in some typical processes, dry mill ethanol production utilizes the starch portion of corn kernels (which typically comprises 70% by weight of the kernel) wherein the starch component is converted by enzymatic hydrolysis to sugars that are then fermented to form ethanol. The ethanol is recovered by distillation leaving a still bottoms fraction comprising high levels of cellulosic-based fiber and unconverted, inaccessible, starch bound thereto. The still bottom fraction may be processed to form distillers grain that is typically used as ruminant animal feed due to the high fiber content.

In conventional starch to ethanol processes, the energy crop (typically a grain such as #2 yellow dent corn, wheat, barley or milo) is ground and slurried with process water and/or backset to form a mash. α-amylase enzyme is added to liquefy the mash and begin hydrolyzing accessible starch to long chain dextrins. In some processes, the starch slurry is heated using a hydroheater or in a stirred tank to gelatinize granular starch, before or after adding the α-amylase enzyme, and the heated gelatinized slurry is forwarded to liquefaction tank to finish starch hydrolysis and form a liquefied mash. In some other processes, termed "non-cooking processes" the starch slurry is not heated. In any such process, additional α-amylase enzyme may be added to hydrolyze the gelatinized starch to short chain dextrins. The liquefied mash is then cooled to a temperature in the range of 30° C. to 35° C. and the pH is adjusted to within a range of 4 to 5 whereupon glucoamylase is added to form fermentable hexose monosaccharides (e.g., glucose) from dextrins. Yeast is then added to convert the hexose to ethanol. In some processes, glucoamylase and yeast are added simultaneously or in close sequence to form ethanol from glucose in a simultaneous saccharification and fermentation process ("SSF").

Problematically, in such processes, cellulose contained in the fiber component and starch bound thereto (i.e., inaccessible starch) are not converted to fermentable sugar. Some prior art processes attempt convert cellulose and bound starch to fermentable sugar (i) by adding cellulase enzyme and, optionally, glucoamylase enzyme, to the mash during the liquefaction step or (ii) by adding cellulose enzyme to the liquefied mash during saccharification, fermentation or during SSF. This approach suffers from several drawbacks. For instance, the normal conditions for saccharification and fermentation (e.g., 30° C. to 35° C. and pH 4 to 5) are not optimal for cellulase enzyme activity. An alternative is to perform cellulose hydrolysis at the optimal conditions of from 50° C. to 55° C. and pH 5, but this option is costly because the entirety of the mash must be conditioned resulting in high capital costs. Moreover, extended cycle time and reduced throughput due to long mixing and residence times required to effective hydrolysis renders such an approach commercially impractical. Furthermore, in any such process, cellulase enzyme is significantly diluted because of the low fiber concentration in the mash slurry which results in high loss of enzyme activity over time, and certain components in the mash, such as oil, interfere with cellulase activity.

Accordingly, a method for improving the yield of ethanol from energy crops by converting cellulose and inaccessible starch to fermentable sugar is desirable.

BRIEF DESCRIPTION OF THE INVENTION

The present invention generally relates to processes for production of ethanol from energy crops including, improved methods for fractionating liquefied mash, improved efficiency of conversion of energy crop cellulosic components to monosaccharides, and improved yield of ethanol from energy crops.

In another aspect, a process for preparing a composition comprising glucose from an energy crop is provided. The process comprises forming a mashing mixture comprising a milled energy crop, water and an alpha-amylase enzyme; forming a liquefied mash from the mashing mixture, the liquefied mash comprising (i) coarse insoluble particles comprising cellulose, (ii) non-liquefied starch, (iii) fine insoluble particles and (iv) liquefied starch; and forming an adjusted liquefied mash by adjusting the liquefied mash to a pH suitable for hydrolysis of cellulose by cellulose enzymes. The adjusted liquefied mash is fractionated to form (i) a coarse fraction comprising greater than 50% by weight of the coarse insoluble particles contained in the adjusted liquefied mash and greater than 50% by weight of the non-liquefied starch contained in the adjusted liquefied mash and (ii) a fine fraction comprising greater than 50% by weight of the fine insoluble particles contained in the adjusted liquefied mash and greater than about 50% by weight of the liquefied starch contained in the adjusted liquefied mash. At least a portion of the coarse fraction is admixed with at least one cellulase enzyme to form a coarse fraction hydrolyzate. At least a portion of the coarse fraction hydrolyzate is admixed with at least a portion of the fine fraction to form a combined liquefied admixture, (ii) a glucoamylase enzyme is added to the combined liquefied admixture, and (iii) the combined liquefied admixture is saccharified to form the composition comprising glucose.

BRIEF DESCRIPTION OF THE DRAWINGS

FIG. 1 depicts the process flow of one embodiment of a process of the present invention.

DETAILED DESCRIPTION OF THE INVENTION

The present invention is generally directed to conversion of energy crops to ethanol by fermentation. Described herein are improved processes for production of ethanol from energy crops including, for example, processes which provide improved ethanol yield. Also described herein are processes which provide various advantageous co-products. As detailed herein, improvements in ethanol yield and/or advantageous co-products may be provided by one or more aspects of various protocols for treatment of the fiber component of energy crops to generate fermentable sugars that may be utilized by fermentation organisms in an ethanol production process.

In some aspects of the present invention, the process improves the conversion of starch into fermentable sugars, which may thereby enhance the efficiency of the fermentation of starch-derived sugars from an energy crop to ethanol. In other aspects, the process of the present invention enables the conversion of complex cellulosic polysaccharides into fermentable sugars, which may then be fermented into ethanol. In conventional processes, these complex polysaccharides (e.g., cellulose, hemicellulose, and other fibers such as lignin-cellulose complex and lignin-hemicellulose complex) typically provide little or no fermentable sugar substrate to the ethanol fermentation process, and are typically purged from the process as a component of whole stillage or as distillers grains. Accordingly, in some aspects of the process of the present invention, at least a portion of these complex polysaccharides are isolated and converted to fermentable sugars. The fermentable sugars may then be converted to ethanol thereby enhancing the ethanol yield.

Some other aspects of the present invention are directed to a process for forming an improved feed co-product derived from ethanol fermentation of an energy crop. By converting at least a portion of complex polysaccharides in the energy crop into fermentable sugars and fermenting at least a portion of the fermentable sugars to ethanol, the process of the present invention yields a whole stillage feed co-product (e.g., distillers grain) comprising enhanced concentrations of components of high nutritional quality (e.g., protein and oil) and having reduced concentrations of complex polysaccharides of comparatively less nutritive value (e.g., hemicellulose and cellulose). The present invention is therefore further directed to a feed co-product having enhanced nutritive value as compared to the grain feed products currently available from the commodity markets.

Various processes for processing energy crops to improve the yield of fermentable sugars are within the scope of the present invention. Generally, the processes comprise fractionating a liquefied energy crop at temperature and pH conditions favorable for cellulase activity into a coarse fraction comprising a majority of the fiber component and a majority of the non-liquefied starch and a fine fraction comprising a majority of the liquefied starch. As used herein "majority" and "predominantly" mean greater than 50%, 60%, 70%, 80%, 90% or 95% of any of a population %, w/w %, w/v % or v/v % basis. The coarse fraction is contacted with a source of enzymes comprising at least one cellulase enzyme to hydrolyze at least a portion of the cellulose to fermentable hexose monosaccharide sugars (e.g., glucose) and to free inaccessible starch bound thereto. The hydrolyzed coarse fraction and fine fraction are combined and thereafter contacted with a source of enzymes comprising a glucoamylase enzyme to generate fermentable sugars comprising hexose monosaccharides (e.g., glucose).

Various other aspects of the present invention involve enzymatic conversion of other coarse fraction components to fermentable sugars and/or other fermentation aids. For instance, α-amylase enzyme can be added to the coarse fraction to liquefy starch that was previously bound to the fiber. Further, at least one hemicellulase enzyme can be added to the coarse fraction to covert hemicellulose to pentose monosaccharide sugars (e.g., xylose). Yet further, protease enzymes can be added to the coarse fraction to hydrolyze and cleave protein to peptides and amino acids thereby releasing bound starch granules and providing usable sources of free amino nitrogen that are believed to enhance the efficiency of the fermentation organism.

Various other aspects of the present invention involve acid pretreatment of the energy crop mash prior to liquefaction to convert cellulose to fermentable hexose monosaccharide sugars (e.g., glucose) and hemicellulose to fermentable pentose monosaccharide sugars (e.g., xylose).

Still other aspects of the present invention involve converting the hexose monosaccharide sugars to ethanol with an ethanol fermentation organism source comprising at least one species of an organism capable of converting hexose sugars to ethanol. Various other aspects involve converting pentose sugars to ethanol with an ethanol fermentation organism source comprising at least one species of an organism capable of converting pentose sugars to ethanol. Still other aspects involve converting hexose monosaccharides and pentose monosaccharides to ethanol with an ethanol fermentation organism source comprising at least one species of an organism capable of converting both hexose sugars and pentose sugars to ethanol. Various other aspects of the present invention are directed to converting cellulose or hemicellulose to ethanol with an ethanol fermentation organism source comprising at least one species of a cellulolytic organism capable of converting cellulose to ethanol and/or at least one species of a cellulolytic organism capable of converting hemicellulose to ethanol. Other aspects of the present invention are directed to the fermentation of a combined liquefied admixture comprising hexose monosaccharides, pentose monosaccharides, cellulose and hemicellulose with an ethanol fermentation organism source comprising at least one species of an organism capable of converting hexose sugars to ethanol, at least one species of an organism capable of converting pentose sugars to ethanol, and at least one species of a cellulolytic organism capable of converting complex carbohydrates to ethanol. Other aspects of the present invention are directed to the fermentation of a combined liquefied admixture comprising hexose monosaccharides, pentose monosaccharides, cellulose and hemicellulose with an ethanol fermentation organism source comprising at least one species of an organism capable of converting hexose sugars and pentose sugars to ethanol and at least one species of a cellulolytic organism capable of converting complex carbohydrates to ethanol.

In any of the various aspects of the present invention, the process generally comprises forming a fermentable sugar composition comprising glucose. In a first step, an aqueous mashing mixture comprising an energy crop and an α-amylase enzyme is formed. The aqueous mashing mixture is liquefied to form a liquefied mash. The liquefied mash comprises a coarse fraction and a fine fraction. The coarse fraction comprises a majority of the insoluble cellulose particles and a majority of the non-liquefied starch. The fine fraction comprises a majority of the fine insoluble particles and a majority of the liquefied starch. An adjusted liquefied mash is formed by adjusting the pH of the liquefied mash to conditions suitable for hydrolysis of cellulose by cellulase. The adjusted liquefied mash is then fractionated to form (i) a coarse fraction comprising greater than 50% by weight of the coarse insoluble particles contained in the adjusted liquefied mash and greater than 50% by weight of the non-liquefied starch contained in the adjusted liquefied mash and (ii) a fine fraction comprising greater than 50% by weight of the fine insoluble particles contained in the adjusted liquefied mash and greater than about 50% by weight of the liquefied starch contained in the adjusted liquefied mash. The coarse fraction is then combined with a cellulase enzyme to form a coarse fraction hydrolyzate comprising cellulose-derived hexose sugars and unbound starch. At least a portion of the coarse fraction hydrolyzate is combined with at least a portion of the fine fraction to form a combined liquefied admixture. A glucoamylase enzyme is added to the combined liquefied admixture to form the sugar composition. In some other aspects of the present invention, at least one species of ethanol fermentation organism is added to the sugar composition to form a soluble sugar fermentation mixture. The fermentation mixture is then fermented to form a beer composition comprising ethanol. Other aspects within the scope of the present invention are described herein.

One aspect of the present invention is depicted in FIG. 1. In summary, milled grain 1 is combined with water 2 and a source of α-amylase enzyme 3 in a liquefaction step 10 to form a liquefied mash 15. In a conditioning step 20, the liquefied mash 15 is adjusted to a pH suitable for cellulase activity by pH adjustment with the acid 21 to form conditioned liquefied mash 25. In a fractionation step 30, the adjusted liquefied mash 25 is processed, such as through a filtration media, to form a fine fraction stream 31 (undersize) and a highly viscous coarse fraction stream 32 (oversize). In a viscosity reduction step 40, the highly viscous coarse fraction stream 32 is combined with a source of cellulase enzyme 41 to form a reduced viscosity coarse fraction stream 45. The reduced viscosity coarse fraction stream 45 is transferred to a hydrolysis reactor for completion of hydrolysis in a cellulose hydrolysis step 50 to generate a coarse fraction hydrolyzate 55. In a cooling and mixing step 60, at least a portion of the coarse fraction hydrolyzate 55 is admixed with at least a portion of the fine fraction stream 31 and a source of a starch hydrolyzing enzyme 61 to form a combined liquefied admixture 65 comprising fermentable sugar. In a saccharification and fermentation step 70, the combined liquefied admixture 65 is admixed with a source of yeast 71 for generation of ethanol from the fermentable sugar resulting in a beer stream 75. In a distillation step 80, the beer stream 75 is processed to form ethanol 81 and whole stillage 82.

Energy Crop Feedstock

The feedstock is preferably a plant-based feedstock derived from an energy crop having significant starch content. As is known in the art, an energy crop is a plant whose fruits and/or seeds may be used in the production of biofuels. Examples of energy crops include corn, maize, oats, millet, grain sorghum, milo, wheat, rye, barley, triticale, rice, buckwheat, bamboo, potatoes, cassava, sweet potato, yam, sugar beet, sugar cane, and combinations thereof. The fruits and/or seeds of an energy crop typically comprise a large portion of starch, which is readily fermentable into ethanol by conventional processes. The feedstock used in the process of the present invention may be any feed stock comprising at least about 40% by weight, preferably at least about 50% by weight of a carbohydrate, such as a starch or sugar, which is fermentable into ethanol. A corn kernel, for example, typically comprises about 70% by weight starch on a dry basis. Sorghum (milo) also contains about 70% by weight starch. Wheat contains about 65% by weight starch. Rye contains about 58% by weight starch. Barley contains about 51% by weight starch. In addition to starch, the energy crops further comprise other components including protein, oil, and complex polysaccharides including cellulose, hemicellulose, lignocellulose complex and ligninhemicellulose complex. For instance, corn kernels typically comprise from about 2 to about 4 percent by weight cellulose and from about 5 to about 7 weight percent hemicellulose.

Starches typically comprise two components: amylose and amylopectin. Amylose is a polysaccharide that may comprise up to several thousand glucose units, more typically comprising from about 300 to about 3000 glucose units in alpha linkages. Amylose is characterized by relatively little branching, such that the main linkage is α(1→4), which promotes formation of a helical structure. Amylopectin is a polysaccharide typically comprising from about 2000 to about 20,000 glucose units in alpha linkages. Unlike amylose, amylopectin is highly branched and comprises linear portions in α(1→4) linkages with branching taking place through α(1→6) linkages at about every 24 to 30 glucose units. Plants store amylopectin and amylose as starch granules in amyloplasts.

Of the complex carbohydrates, cellulose is a major component of energy crops, and is a structural, linear polysaccharide of the plant cell wall containing anywhere from several hundred to over ten thousand glucose units in β(1→4) linkages. Hemicelluloses are random, amorphous, heteropolymers also present in cell walls, typically comprising about 200 saccharide units, and comprise various polysaccharides formed from the hexose sugars glucose, mannose, galactose and rhamnose and the pentose sugars xylose and arabinose. Hemicellulose is typically covalently linked to lignin, a complex, cross-linked, polymeric macromolecule that fills the spaces in cell walls between the cellulose, hemicellulose, and pectin components. Since hemicellulose is a random, amorphous polymer, it provides little strength and is easily hydrolyzed by dilute acid or base and a variety of hemicellulase enzymes.

The energy crop feedstock may be whole dry grind grain. The energy crop may also suitably comprise various energy crop fractions generated in wet milling processes known in the art. In some optional aspects of the present invention, the energy crop feedstock may comprise various streams or components generated in dry fractionating processes.

Dry milled energy crops are generally prepared by milling the raw plant matter (i.e., the seed and/or fruit of the energy crop) into flour (also termed "meal"), typically using a hammer mill with screening, a roller mill or a ball mill. In the case of a hammer mill, in some aspects, a screen size opening of from about 2 mm to about 5 mm, for example, about 3 mm is used wherein typical milled energy crop feedstock particle size is generally characterized as less than about 35%, less than about 40%, less than about 45%, less than about 50%, less than about 60%, less than about 70%, less than about 80% or even less than about 90% of the milled material passes through a 0.5 mm to 1 mm sieve opening. In some other hammer mill aspects, a screen size opening of from about 01 mm to about 2 mm is used wherein typical milled energy crop feedstock particle size is generally characterized as having greater than about 50%, greater than about 60%, greater than about 70%, greater than about 80% or even greater than about 90% of the milled material passes through a sieve opening of from about 0.1 mm to about 0.5 mm. In some aspects, the grain is dry milled into a flour or meal wherein a plurality of the particles have an average particle size of about 250, about 500, about 750, about 1000, about 1250, about 1500, about 1750 or about 2000 micrometers, and ranges thereof, such as from about 250 micrometers to about 1250 micrometers, or from about 500 micrometers to about 750 micrometers. In some aspects, the meal is processed without separating out the various component parts of the grain such that the flour comprises all of the grain components, including the protein, starch, fibers (e.g., cellulose, hemicellulose and lignocellulose), and oil. In some aspects of the present invention, the feedstock is a dry milled corn.

Wet milled energy crops are typically prepared by first soaking or steeping the grain in an aqueous based medium, for instance, in sulfurous acid, to soften the grains and allow wet grinding to release the oil-containing germ and coarse fiber from the endosperm. The fiber and germ are separated and, in some wet milling processes, the endosperm is further processed and separated into starch and protein fractions. The separated starch streams from wet-milling can advantageously serve as a feedstock to the ethanol fermentation process due to the reduced amount of non-fermentable matter entering the process and the ability to capture the oil, protein, and fiber separately which have economic value for human food and other applications. See, McFate, U.S. Pat. No. 3,236,740. Wet milling is preferably done to a fine grind in order to enhance the separation of protein from starch in the cooking step.

Energy crops may also be processed by dry fractionation. For instance, in some such processes, corn kernels may be processed to separate an endosperm fraction (comprising a majority of the starch) from a germ fraction (comprising a majority of the protein and oil) and a hull (bran) fraction (comprising a majority of the complex carbohydrates, or fiber). Separation methods are known in the art and include (i) energy crop cracking in combination with size separation and (ii) grain dehulling/debranning machines such as commercially available from Buhler Ltd. and Satake USA. The germ fraction is typically processed to recover oil and the endosperm fraction is typically used as a fermentation substrate.

In yet some other optional aspects of the present invention, the energy crop feedstock may comprise energy crop meal (e.g., corn meal) that is generated in oil extraction processes known in the art wherein a ground and/or flaked energy crop is extracted with a solvent or pressed to generate an oil fraction and a meal fraction.

Aqueous Mashing Mixture

In the process of the present invention, an aqueous mashing mixture is formed comprising (i) milled or processed energy crop, (ii) at least one source of α-amylase enzyme and (iii) water, thin stillage, whole stillage, a condensate of thin stillage, a condensate of whole stillage, or combinations thereof.

In some aspects of the present invention, the aqueous mashing mixture is formed by mixing milled or processed energy crop feedstock, water, and whole stillage. Whole stillage may comprise between about 8% and about 20% dry matter by weight ("wt. %"), more typically from about 9.5 wt. % to about 14 wt. %, more typically from about 12 wt. % to about 14 wt. %. As described in more detail herein, whole stillage is a feed co-product derived from the ethanol fermentation of the grain of an energy crop. Optionally, whole stillage from a prior batch may be recycled. Whole stillage comprises a portion of residual starch that was, for one reason or another, not fermented by yeast into alcohol. By using whole stillage backset to prepare the mashing mixtures, the process of the present invention enhances the conversion of starch into alcohol, thereby improving ethanol yield per a given mass of plant feedstock.

In some other aspects, the aqueous mashing mixture is formed by mixing milled or processed energy crop feedstock, water, and thin stillage. As described in more detail herein, thin stillage is a feed co-product obtained by the separating coarse solids (i.e., the wet distillers grains, which contains from about 25 wt. % to about 35 wt. % dry matter (solubles)) from the aqueous portion of whole stillage by, for example, centrifugation. Thin stillage typically comprises about 5 wt. % dry matter (solubles).

Condensates of whole stillage may also be recycled into the process at this stage, including modified wet distillers grains plus solubles having about 50% dry matter by weight and wet distillers grains plus solubles having about 25% to about 3% dry matter by weight. Condensates of thin stillage (known as condensed distillers solubles) having from about 23% to about 45% dry matter by weight may also be recycled into the process at this step.

In some other aspects, un-dried distillers grains, dried distillers grains ("DDG"), un-dried distillers grains plus solubles or dried distillers grains plus solubles ("DDGS") may be recycled to form the mash in the process of the present invention.

Combinations of water, thin stillage, whole stillage, thin stillage condensate, whole stillage condensate, distillers grain (dried or un-dried) and/or distillers grain plus solubles (dried or un-dried) may be used to form the aqueous mashing mixture.

The relative proportions of the components of the aqueous mashing mixture, e.g., dry milled or wet milled feedstock, water, and, optionally, recycled whole stillage, thin stillage, condensates of whole stillage, condensates of thin stillage, distillers grain (dried or un-dried) and/or distillers grain plus solubles (dried or un-dried), are selected such that the aqueous mashing mixture comprises a solids content of about 15 wt. %, about 20 wt. %, about 25 wt. %, about 30 wt. %, about 35 wt. % or about 40 wt. %, and ranges thereof, such as from about 15 wt. % to about 45 wt. %, from about 20 wt. % to about 40 wt. %, or from about 30 wt. % to about 37 wt. %, such as about 32 wt. %, about 33 wt. %, about 34 wt. %, or about 35 wt. %. In one aspect of the present invention, at least about 25%, for example about 25%, about 50%, about 75%, about 90%, or even 100% of the water added to the mix tank can be replaced with thin stillage, whole stillage, condensates of thin stillage and/or condensates of whole stillage (collectively referred to as backset). Increased fermentation production rates are generally positively correlated with backset addition. Under one theory, and without being bound to any particular theory, it is believed that backset provides at least a portion of the essential yeast nutrients and micronutrients, and serves as a pH buffer. In one backset addition option, less than complete backset recycle is used, such as from about 25% to about 75% backset addition to the mix tank, in order to purge a portion of the fermentation impurities and inhibiters from the process. In some other backset aspects, the backset comprises less than about 50%, about 40%, about 30%, about 20% or even less than about 10% combined whole stillage and condensates of whole stillage.

The pH of the aqueous mashing mixture is adjusted to from about 5 to about 6.5, from about 5.5 to about 6.5, or from about 5.5 to about 6 with a suitable acid or base, as necessary. Examples of suitable bases include ammonia and sodium hydroxide, and examples of suitable acids include sulfuric acid and hydrochloric acid.

In the next step of the process according to the present invention, a thermally stable α-amylase enzyme is added to the aqueous mashing mixture. α-amylase hydrolyzes the starch chains at random locations to effect cleavage of α(1→4) glucosidic linkages and break down long chain carbohydrates, ultimately yielding (i) non-retrograding sugars, such as maltotriose and maltose from amylose (reduction of amylose can be measured using iodine staining) and (ii) maltose, glucose, maltodextrins and "limit dextrin" (low MW carbohydrates containing the α(1→6) linkages, which are not hydrolyzed by α-amylase) from amylopectin. Retrogradation is recrystallization that occurs during cooling, which makes starch resistant to fermentation. Examples of typical bacterial and fungal α-amylases include, for example, enzymes derived from *B. licheniformis, B. amyloliquefaciens, B. stearothermophilus, Aspergillus oryzae* and *Aspergillus niger*. α-Amylase enzyme is available commercially, such as from Novozymes, Liquozyme, CDS, Genencor, among other sources. Examples of commercial acid α-amylases suitable for use in the present invention include TERMAMYL® SC, LIQUOZYME® SC DS, LIQUOZYME® SC 4X, and SAN™ SUPER (all available from Novozymes AJS, Denmark); and DEX-LO®, SPEZYME® FRED, SPEZYME® AA, and SPEZYME® DELTAAA (all available from Genencor). Typical enzyme loadings include about 0.01 wt. %, about 0.05 wt. %, about 0.1 wt. %, about 0.2 wt. %, about 0.3 wt. %, about 0.4 wt. % or about 0.5 wt. % based on the dry weight of the mashing mixture solids, and ranges thereof, such as from about 0.01 wt. % to about 0.5 wt. % or from about 0.1 wt. % to about 0.4 wt. %.

Liquefied Mash

The aqueous mashing mixture is heated to form a liquefied mash comprising non-liquefied starch, fine insoluble particles, liquefied starch, and coarse insoluble particles comprising cellulose. The temperature of the aqueous medium may be elevated with indirect heat, or more typically, cooked with direct steam injection, such as by jet cooking. An example of a suitable commercial jet cooker is a Hydroheater®. In jet cooking, the starch is generally liquefied by a combination of heat and the steam-induced shear and mechanical forces that gelatinize or "paste" the starch (i.e., swells the starch granules with water to hydrate the amylase and amylopectin chains) and destroys the crystalline structure, thereby rendering the starch amenable to enzymatic attack. Jet cooking may further hydrolyze the starch chains. It will be appreciated that the temperature, pressure, and residence time are interdependent so that the modifications in any of those variables may be made in order to accommodate the heat liquefaction process into the fermentation process.

In some aspects of the present invention, jet cooking may occur at a temperature of at least about 85° C., or at least about 100° C., such as from about 100° C. to about 200° C., from about 120° C. to about 160° C., from about 140° C. to about 160° C., from about 90° C. to about 110° C., from about 95° C. to about 110° C. or from about 100° C. to about 110° C. In some other aspects, jet cooking may occur at a temperature of about 70° C., about 75° C., about 80° C., about 85° C., about 90° C., about 95° C., about 96° C., about 97° C., about 98° C., about 99° C., about 100° C., about 101° C., about 102° C. or about 103° C., or ranges thereof, such as from about 70° C. to about 103° C., or from about 80° C. to about 100° C. Direct steam injection generally disperses the aqueous mixture into mist. To disperse the aqueous mixture into mist, the aqueous medium is preferably pumped into the jet cooker at a pressure of at least about 300 kPa (about 45 psi), at least 350 kPa (about 50 psi), at least 400 kPa (about 58 psi), or at least about 410 kPa (about 60 psi), and forced through a jet of high velocity steam introduced into the jet cooker at a pressure of at least 800 kPa (about 115 psi), at least 900 kPa (about 130 psi), at least about 1000 kPa (about 145 psi), at least about 1025 kPa (about 148 psi), or at least about 1035 kPa (about 150 psi). The jet cooker preferably has a back pressure of at least about 25 kPa (about 4 psi), at least about 40 kPa (about 6 psi), at least about 50 kPa (about 7 psi) or at least about 75 kPa (about 10 psi), as needed, to prevent flashing. In the jet cooker, the pressure of the aqueous mixture typically drops by from about 200 kPa (about 30 psi) to about 325 kPa (about 50 psi), or from about 250 kPa (about 35 psi) to about 300 kPa (about 45 psi), such as about 275 kPa (about 40 psi). The pressure of the steam drops by at least about 700 kPa (about 100 psi), at least about 800 kPa (about 115 psi), such as at least about 850 kPa (about 125 psi), or about 900 kPa (about 130 psi). The pressure drop of the steam and the liquid mixture assists in dispersing the fluid mixture into a mist in the jet cooker. Jet cooking at elevated temperature may occur for from about 5 minutes to about 20 minutes, such as about 10 minutes.

In some optional aspects of the present invention, the liquefaction process is continuous and the α-amylase enzyme is added to a heat-liquefied mash suspension as it exits the jet heater wherein it is transferred to a plug flow vessel that provides sufficient residence time for hydrolysis. In some aspects, the heat-liquefied mash suspension passes from the jet heater into one or more holding vessels, such as a horizontal tank, having sufficient volume to provide a residence time of from about 30 minutes to about 2 hours at a temperature of from about 55° C. to about 90° C. In one aspect, during the digestion step, the heat-liquefied mash suspension is treated with additional α-amylase enzyme in a second enzyme stage, alone or in combination with one or more other enzymes such as glucoamylase, β-amylase, pullulanase, glucose isomerase or protease, sequentially or in combination. In another aspect, the liquefaction process is semi-continuous and the heat-liquefied mash suspension is fed from the jet heater to a hold tank for batch-wise digestion and/or second stage enzymatic treatment. In yet another aspect, the pre-liquefied mash suspension is heated and digested (optionally including a second enzyme stage) in a batch process in one vessel or a series of vessels. If thermostable α-amylase enzyme is used alone in the second enzyme stage, the temperature will preferably range from about 80° C. to about 110° C., for example about 85° C. If other enzymes are present such as glucoamylase, the temperature is preferably somewhat lower, for example, about 55° C. to about 75° C. Typical α-amylase enzyme dosages are described above.

In some optional aspects of the present invention, the liquefied mash is formed from an aqueous mashing mixture in a process comprising the steps including (i) heating under acid conditions in the absence of α-amylase enzyme, (ii) pH adjustment, if necessary, to from about 5 to about 6.5, and (iii) treatment thereof with α-amylase enzyme.

In an optional acid-pretreatment first step, a mashing mixture is heated under acid conditions with agitation in the absence of α-amylase enzyme. More particularly, prior to inoculation of the aqueous mashing mixture with a thermally stable α-amylase enzyme, the aqueous mashing mixture is subjected to acid hydrolysis under generally mild conditions of pH and temperature. To prepare the mash for acid hydrolysis, the pH of the mash may be adjusted to about 2, about 2.5, about 3, about 3.5, about 4, about 4.5, about 5, about 5.5 or about 6, and ranges thereof, such as from about 2 to about 6, from about 2 to about 5.5, or from about 2 to about 4. In some aspects, the pH is about 2.5, about 4, or about 5. For acidic pH adjustment, if necessary, sulfuric acid, hydrochloric acid, acetic acid, lactic acid, citric acid, tartaric acid, and the like, may be used. If necessary, for alkaline pH adjustment, ammonia, sodium hydroxide and potassium hydroxide, are suitable. Acid hydrolysis may be done at a temperature below about 65° C. or below about 55° C. (which is about the gelation point of starch). In some aspects the acid hydrolysis temperature is from about 45° C. to about 55° C. In some other aspects the acid hydrolysis may be done at room temperature. The liquid mash may be agitated by conventional means. Acid hydrolysis may occur under these mild conditions, for example, for a duration of between about five minutes and about 120 minutes, although longer durations, such as 3, 4, or 5 hours or longer, are within the scope of the present invention.

After the period of acid hydrolysis at mild temperature, acid hydrolysis may optionally then be done at elevated temperature as described above, such as by jet cooking. Jet cooking under acidic conditions solubilizes and gelatinizes the amylose and branched amylopectin chains of the starch and makes them available for enzymatic hydrolysis. Moreover, jet cooking thins the material at the temperature at which the material is introduced into the enzymatic reactor. The acidic conditions also hydrolyze at least a portion of the amylose and amylopectin, yielding glucose oligomers. The acidic conditions also serve to condition the cell walls and further enhance the release and availability of the starch. In addition, the acidic and high temperature conditions in the cooking step breaks down lignin-hemicellulose complexes and may hydrolyze the hemicellulose, thereby producing soluble oligomers and monomers of the pentose sugars xylose and arabinose, and other sugars. The pentose ("C5") sugars such as xylose and arabinose comprise the majority of the sugars released from hemicellulose hydrolysis. In this aspect, prior to inoculation of the aqueous medium comprising gelatinized starch with the thermally stable α-amylase enzyme, the mixture is cooled to a temperature of from about 70° C. to about 90° C., such as about 85° C. The gelatinized medium may optionally be flashed cooled to the desired temperature. If necessary, the pH of the gelatinized medium is adjusted to from about 4 to about 6.5, from about 4.5 to about 6.5, or from about 5 to about 6.5 prior to α-amylase addition.

In a second step, to initiate liquefaction, the gelatinized medium is inoculated with α-amylase typically to a concentration as described above based on the dry weight of the solids. α-amylase inoculation may occur by batchwise or continuous addition. For instance, the gelatinized medium may be inoculated in a vessel that may be a holding tank for batchwise addition or the vessel may be a stretch of pipe or a horizontal tank that allows near plug-flow of the medium during continuous α-amylase inoculation. The relative rates of flow of α-amylase and mash are controlled so that the composition in the mixture is maintained within the preferred range of initial conditions.

In any of the various aspects of the present invention, the enzyme inoculate is allowed to liquefy the mash for a duration typically of from about 1 to about 4 hours, such as about 3 hours, which is generally sufficient form a liquefied mash having a dextrose equivalent (DE) in the range of from about 10 to about 30, from about 10 to about 20, or from about 12 to about 15.

The liquefied mash comprises coarse particles comprising fibers such as cellulose, hemicellulose, and lignocellulose. A plurality of the coarse particles are characterized as having an average particle size of at least about 300 microns, at least about 350 microns, at least about 400 microns, at least about 450 microns, at least about 500 microns, at least about 600 microns, at least about 700 microns, at least about 800 microns, at least about 900 microns, or at least about 1000 microns. The liquefied mash further comprises non-liquefied starch particles, wherein a plurality of starch particles are characterized as having a particle size of at least about 300 microns, at least about 350 microns, at least about 400 microns, at least about 450 microns, at least about 500 microns, at least about 600 microns, at least about 700 microns, at least about 800 microns, at least about 900 microns, or at least about 1000 microns. The coarse fraction comprises a majority of the coarse particles and non-liquefied starch particles wherein the liquefied mash comprises about 15 wt. %, about 20 wt. %, about 25 wt. %, about 30 wt. %, about 35 wt. %, about 40 wt. % or about 45 wt. %, and ranges thereof, such as from about 15 wt. % to about 45 wt. %, or from about 20 wt. % to about 40 wt. %, of the coarse fraction. The liquefied mash yet further comprises liquefied starch and fine insoluble particles, wherein a plurality of the fine insoluble particles have a particles size of less than about 1000 microns, less than about 900 microns, less than about 800 microns, less than about 700 microns, less than about 600 microns, less than about 500 microns, less than about 450 microns, less than about 400 microns, less than about 350 microns, less than about 300 microns, less than about 250 microns, less than about 200 microns, less than about 150 microns or less than about 100 microns. The fine fraction comprises a majority of the liquefied starch and fine insoluble particles, wherein the liquefied mash comprises about 55 wt. %, about 60 wt. %, about 65 wt. %, about 70 wt. %, about 75 wt. %, about 80 wt. % or about 85 wt. %, and ranges thereof, such as from about 55 wt. % to about 85 wt. %, or from about 60 wt. % to about 80 wt. %, of the fine fraction.

The relative proportions of the coarse and fine fractions, the average particle size and the size distribution are a function of at least the energy crop source, particle size thereof, processing methods and conditions, fractionation method (described below) and size exclusion device (e.g., screen mesh size or hole diameter as described below). In aspects of the present invention wherein size exclusion is used, those skilled in the art will recognize that the media size (e.g., screen mesh) generally provides a cut-off where the particle size of the oversize material is generally at least that of the opening and the particle size of the undersize material is at least that of the opening. In aspects of the present invention where separation by density is used (e.g., centrifugation), those skilled in the art will recognize that the resultant average separated particle size of the coarse and fine fractions is a function of particle density, applied gravitational force, viscosity and size exclusion device, if used (such as with a basket-type centrifuge). In some aspects of the present invention, the weight ratio of the coarse fraction to the fine fraction is about 1:6, about 1:5, about 1:4, about 1:3, about 1:2, about 1:1.5 or about 1:1.2, and ranges thereof, such as from about 1:6 to about 1:1.2, from about 1:5 to about 1:1.5, or from about 1:4 to about 1:2. In some aspects of the present invention, a plurality of coarse insoluble particles has a particle size in excess of about 300 microns and a plurality of fine insoluble particles has a particle size of less than about 300 microns, a plurality of coarse insoluble particles has a particle size in excess of about 400 microns and a plurality of fine insoluble particles has a particle size of less than about 400 microns, a plurality of coarse insoluble particles has a particle size in excess of about 500 microns and a plurality of fine insoluble particles has a particle size of less than about 500 microns, a plurality of coarse insoluble particles has a particle size in excess of about 700 microns and a plurality of fine insoluble particles has a particle size of less than about 700 microns, or a plurality of coarse insoluble particles has a particle size in excess of about 1000 microns and a plurality of fine insoluble particles has a particle size of less than about 1000 microns.

The liquefied mash is adjusted to pH conditions suitable for the action of cellulase enzyme on cellulose. More particularly, the pH is preferably adjusted to from about 4 to about 5.5 or from about 4.5 to about 5. In some aspects of the present invention, the temperature of the adjusted liquefied mash is reduced to from about 85° C. (liquefying temperature) to about 65° C., to about 60° C., or to about 55° C. prior to fractionation. It has been discovered that adjustment to within a pH and temperature range preferred for cellulose hydrolysis by cellulase reduces the liquefied mash viscosity thereby enabling for more efficient fractionation as compared to fractionation at a pH or temperature falling outside that range.

Fractionation

The adjusted liquefied mash is fractionated to form a coarse fraction and a fine fraction. Any size exclusion, size separation or density separation method is generally suitable for the practice of the present invention. Fractionation may be done with a centrifugal sifter, a rotary screen, a trommel, a screening screw conveyor, a vibratory screen, a centrifuge, a pressure screen, or a filter. In some aspects, the adjusted liquefied mash is fractionated by contact with a mesh having a mesh size of about 0.25 mm (Tyler mesh size of 60), about 0.5 mm (Tyler mesh size of 30), about 1 mm (Tyler mesh size of 16), about 1.5 mm (Tyler mesh size of about 12) or about 2 mm (Tyler mesh size of 8), and ranges thereof. In some aspects, the adjusted liquefied mash is fractionated by contact with a perforated screen having a hole diameter of about 0.5 mm, about 1 mm, about 1.5 mm or about 2 mm, and ranges thereof. In any of the various aspects of the present invention, the fine fraction passes through the mesh or perforation as undersize and the coarse fraction is retained on the mesh or perforation as oversize.

The coarse fraction comprises the adjusted liquefied mash fractionated oversize. The coarse fraction comprises greater than 50% by weight of coarse insoluble particles contained in the adjusted liquefied mash, such as about 55%, about 60%, about 65%, about 70%, about 75%, about 80%, about 85% or about 90%, and ranges thereof, such as between 50% and about 90%, from about 55% to about 90%, or from about 60% to about 85%. A plurality of coarse insoluble particles is characterized as having an average particle size as described herein. The coarse insoluble particles comprise energy crop fibrous material and associated inaccessible starch. Fibrous material includes, without limitation, cellulose, hemicellulose and lignocellulose. The relative amount of cellulose, hemicellulose and lignocellulose varies with the energy crop source and the processing methods and conditions. For instance, treatment with acid at elevated temperature prior to α-amylase addition can result in hydrolysis of at least a portion of the fiber resulting in free hexose ("C6") and C5 sugars that pass to the fine fraction, while concomitantly reducing the fiber content in the coarse fraction. Generally, the coarse fraction comprises about 5 wt. %, about 10 wt. %, about 15 wt. % or about 20 wt. %, and ranges thereof, such as from about 5 wt. % to about 20 wt. % or from about 10 wt. % to about 20 wt. %, cellulose and about 10 wt. %, about 15 wt. %, about 20 wt. %, about 25 wt. %, about 30 wt. %, about 35 wt. % or about 40 wt. %, and ranges thereof, such as from about 10 wt. % to about 40 wt. %, from about 15 wt. % to about 35 wt. % hemicellulose. The coarse fraction further comprises greater than 50 wt. % by weight of the non-liquefied starch contained in the adjusted liquefied mash, such as about 55 wt. %, about 60 wt. %, about 65 wt. %, about 70 wt. %, about 75 wt. %, about 80 wt. %, about 85 wt. % or about 90 wt. %, and ranges thereof, such as between 50 wt. % and about 90 wt. %, from about 55 wt. % to about 90 wt. %, or from about 60 wt. % to about 85 wt. %. A plurality of non-liquefied starch particles (or granules) is characterized as having an average particle size as described herein.

In an optional aspect of the present invention, the coarse fraction can be subjected to a particle size reduction step. Particle size reduction can increase the surface area to volume ratio of the coarse insoluble particles and non-liquefied starch particles thereby allowing for improved efficiency of enzymatic action thereon, such as by cellulase, hemicellulase, α-amylase and/or glucoamylase (β-amylase) enzymes. Particle size reduction may also reduce viscosity thereby enabling for more efficient admixture thereof with enzymes. Particle size reducing methods known in the art, such as thermal or mechanical means, are suitable for the practice of the present invention. For instance, in some aspects, particle reduction may be done by the action of cavitation wherein a coarse fraction stream is pumped at a pressure of at least about 250 kPa, 500 kPa, 750 kPa, 1000 kPa, or more, through an orifice wherein a pressure differential is created across the orifice resulting in the production of cavitation bubbles and cavities in the coarse fraction stream on the lower pressure downstream side of the orifice. The coarse fraction stream is then passed to a chamber where the bubbles and cavities collapse under the influence of static pressure, wherein emitted energy ("activation energy") is proportional to said static pressure. The emitted energy results in a dispersion and/or size reduction effect. Activation energies of about 0.2, 0.5, 1.0, 1.5 or 2.0 kJ per kg of coarse fraction stream, and ranges thereof, are within the scope of the present invention. In other aspects, the coarse fraction stream may be passed through an in-line mill. Such mills are known in the art and may be selected to achieve a desired degree of shear and milling efficiency, including emulsification, homogenation, grinding, de-agglomeration and fines solids dispersion. Such mills include rotor-stator mills. Examples of suitable in-line mills include Quadro Ytron® Z Emulsifier mills, Schold® in-line disperser mills, Bematik® colloid mills and Greerco® colloid mills. In any of the various aspects, a plurality of the ground coarse particles have an average particle size of at about 100 microns, about 150 microns, about 200 microns or about 250 microns, and ranges thereof, such as from about 100 microns to about 250 microns, or from about 100 microns to about 200 microns, and a plurality of the particles of the non-liquefied starch have an average particle size of at about 100 microns, about 150 microns, about 200 microns or about 250 microns, and ranges thereof, such as from about 100 microns to about 250 microns, or from about 100 microns to about 200 microns.

The fine fraction comprises the adjusted fractionated liquefied mash undersize. The fine fraction comprises greater than 50% by weight of fine insoluble particles contained in the adjusted liquefied mash, such as about 55%, about 60%, about 65%, about 70%, about 75%, about 80%, about 85% or about 90%, and ranges thereof, such as between 50% and about 90%, from about 55% to about 90%, or from about 60% to about 85%. A plurality of fine insoluble particles is characterized as having an average particle size as described herein. The fine fraction further comprises greater than 50% by weight of the liquefied starch contained in the adjusted liquefied mash, such as about 55%, about 60%, about 65%, about 70%, about 75%, about 80%, about 85% or about 90%, and ranges thereof, such as between 50% and about 90%, from about 55% to about 90%, or from about 60% to about 85%. The fine fraction may further comprise fermentable C5 and C6 monosaccharides.

Coarse Fraction Hydrolysis

The coarse fraction is combined with a source of enzymes comprising at least one cellulase to form a coarse fraction hydrolyzate comprising cellulose-based C6 sugars (e.g., glucose). Cellulases are a class of enzymes produced chiefly by fungi, bacteria, and protozoans that catalyze the cellulolysis (hydrolysis) of cellulose into glucose, cellobiose, cellotriose, cellotetrose, cellopentose, cellohexose, and longer chain cellodextrins. Combinations of the three basic types of cellulases may be employed. For example, endo-cellulases may be added to randomly hydrolyze internal β-1,4,-D-glucosidic linkages in order to disrupt the crystalline structure of cellulose and expose individual cellulose chains. Exo-cellulases may be added to cleave off two units (cellobiose), three units (cellotriose), or four units (cellotetrose) from the exposed chains, while β-glucosidase may be added to hydrolyze these compounds into glucose, which is available for fermentation. Examples of cellulases suitable for use in the present invention include, for example, Cellic® CTec2, Cellic® CTec3, CELLUCLAST®, CELLUZYME®, CEREFLO® and ULTRAFLO® (available from Novozymes A/S), LAMINEX®, SPEZYME®CP (Genencor Int.), and ROHAMENT® 7069 W (Rohm GmbH), and GC-220 (Genencor International). The cellulase enzymes are added in amounts of from about 0.001% to about 2.0% wt. of solids, from about 0.025% to about 1.0% wt. of solids, or from about 0.01% to about 1.0% wt. of solids, such as about 0.001 wt. %, about 0.005 wt. %, about 0.01 wt. %, about 0.05 wt. %, about 0.1 wt. %, about 0.5 wt. %, about 1 wt. %, about 1.5 wt. % or about 2 wt. %. Cellulase loading may suitably vary with coarse fraction cellulose content, but typical loading may be expressed as about 5, about 10, about 15, about 20, about 25, about 30, about 35, about 40, about 45 or about 50, and ranges thereof, such as from about 5 to about 50, from about 10 to about 50, from about 20 to about 50, from about 10 to about 50, from about 10 to about 40, from about 10 to about 30, from about 20 to about 50 or from about 20 to about 40 filter paper units (FPU) per gram of cellulose. Alternatively expressed on a FPU per gram of coarse fraction basis, cellulase loading may be about 0.25, about 0.5, about 1, about 2, about 3, about 4, about 5, or about 10 FPU cellulase per gram of coarse fraction, and ranges thereof, such as from about 0.25 to about 10, from about 1 to about 10, from about 0.25 to about 5, or from about 1 to about 5 FPU cellulase per gram of coarse fraction. On another basis, cellulase loading is about 0.3, 0.6, 1.0 or 2 FPU per gram of solids in the coarse fraction.

Cellulase enzymes may be combined with the coarse fraction by any means known in the art to achieve a substantially homogeneous admixture, including agitated mixing tanks, in line mixers, pug mill mixers, paddle mixers, ribbon mixers, or in liquefaction reactors such as reactors having at least one mixing section and at least one plug flow section. Cellulase is preferably added to the coarse fraction at pH of from about 4 to about 5.5 or from about 4.5 to about 5 and a temperature of from about 35° C. to about 70° C., from about 45° C. to about 65° C., or from about 50° C. to about 55° C.

For highly viscous coarse fractions, mixing can be done in two stages. In a first stage, cellulase can be admixed with the viscous coarse fraction in a mixer particularly suited for the processing of highly viscous materials, for instance, a pug mill mixer, a paddle mixer (single or double shaft), or a ribbon mixer (single or double shaft). High viscosity mixers are particularly suited to the process of the present invention because thorough mixing of cellulase with the viscous coarse fraction enables a rapid viscosity reduction in the hydrolysis step that follows. The high viscosity mixer may optionally have a jacket to receive cooling or heating medium in order to maintain the temperature of the coarse fraction during cellulase addition. In some aspects, cellulase addition can be done through one or more addition points, for example, multiple spray nozzles, positioned near the coarse fraction inlet. In a second stage, the coarse fraction-cellulase admixture may be processed in a mix tank or fiber liquefaction bioreactor. In some aspects, the coarse fraction-cellulase admixture may be processed in a fiber liquefaction bioreactor to further reduce the viscosity prior to transfer to a cellulose hydrolysis reactor. The fiber liquefaction bioreactor may be of either a continuous mixing design or a design and may optionally comprise at least one continuous mixing section and at least one plug flow section. Optionally, two or more fiber liquefaction bioreactors may be operated in series. In some particular aspects, the fiber liquefaction bioreactor comprises alternating mixing zones and near plug flow zones and the coarse fraction-cellulase admixture either flows downward through the tower by gravity or is moved upward by pumping. The coarse fiber-cellulase admixture is typically processed in a fiber liquefaction bioreactor until the admixture viscosity is less than about 8,000 centipoise (cP, less than about 7,000 cP, less than about 6,000 cP, less than about 5,000 cP or less than about 4,000 cP, whereafter it is transferred to a cellulose hydrolysis reactor.

The cellulose hydrolysis reactor is typically an agitated vessel designed to hold the coarse fraction-cellulase mixture at a temperature suitable for cellulose hydrolysis by cellulase wherein the volume is sufficient to provide a hold time to allow for a significant yield of cellulose-derived C6 sugars including, for instance, glucose, dextrose, fructose and levulose. To maintain the temperature inside the hydrolysis reactor, the vessel wall is thermally insulated and/or equipped with heating jacket where heating fluid is circulated through. Glucose yields, based on total cellulose content of the coarse fraction, of at least about 30%, about 40%, about 50%, about 60%, about 70% or at least about 80%, and ranges thereof, such as from about 30% to about 80%, from about 40% to about 80% from about 30% to about 70% or from about 40% to about 70% are preferred. Total cellulose hydrolysis cycle times of 8 hours, 12 hours, 24 hours, 30 hours, 36 hours, 42 hours or 48 hours, and ranges thereof, such as from 8 hours to 48 hours, are within the scope of the present invention.

Optionally, other enzymes such as at least one hemicellulase (e.g., a xylanase), an α-amylase, a β-amylase, a glucoamylase, an arabinoxylanase, a pullanase and/or a protease can be added to the coarse fraction to generate additional C6 sugars, C5 sugars and/or amino acids. The optional enzymes may be admixed with the coarse fraction at any point of hydrolysis including with the cellulase during high viscosity admixing, at one or more locations in the fiber liquefaction bioreactor and/or in the cellulose hydrolysis reactor.

Hemicellulases may be added to further hydrolyze the various types of hemicelloses and to further breakdown the hemicellulose fibers to soluble C5 sugars including xylose and arabinose. A hemicellulase, as used herein, refers to a polypeptide that can catalyze hydrolysis of hemicellulose into small polysaccharides such as oligosaccharides, or monosaccharides including xylose and arabinose. Hemicellulases can be placed into three general categories: the endo-acting enzymes (e.g., endo-1,4-β-D-xylanases) that hydrolyze internal bonds within the polysaccharide (xylan) chain; the exo-acting enzymes (e.g., 1,4-β-D-xylosidases) that act processively from either the nonreducing end of polysaccharide chain and liberate D-xylose residues; and accessory enzymes. Hemicellulases include, for example, the following: endoxylanases, β-xylosidases, α-L-arabinofuranosidases, α-D-glucuronidases, feruloyl esterases, coumarolyl esterases, a galactosidases, β-galactosidases, β-mannanases, and β-mannosidases. Of the accessory enzymes, an α-L-arabinofuranosidase catalyzes the hydrolysis of terminal non-reducing α-L-arabinofuranoside residues in α-L-arabinosides. An α-glucuronidase catalyzes the hydrolysis of an α-D-glucuronoside to D-glucuronate and an alcohol. An acetylxylanesterase catalyzes the hydrolysis of acetyl groups from polymeric xylan, acetylated xylose, acetylated glucose, alpha-napthyl acetate, and p-nitrophenyl acetate. An α-galactosidase catalyzes the hydrolysis of terminal, non-reducing α-D-galactose residues in α-D-galactosides, including galactose oligosaccharides, galactomannans, galactans and arabinogalactans. A β-galactosidase catalyzes the hydrolysis of terminal non-reducing β-D-galactose residues in β-D-galactosides. Such a polypeptide may also be capable of hydrolyzing α-L-arabinosides. A 6-mannanase catalyzes the random hydrolysis of 1,4-β-D-mannosidic linkages in mannans, galactomannans and glucomannans. A β-mannosidase catalyzes the hydrolysis of terminal, non-reducing β D mannose residues in β-D-mannosides. In some aspects, the hemicellulase is an exo-acting hemicellulase, such as an exo-acting hemicellulase which has the ability to hydrolyze hemicellulose under acidic conditions of below pH 7. A xylanase may be obtained from any suitable source, including fungal and bacterial organisms, such as *Aspergillus, Disporotrichum, Penicillium, Neurospora, Fusarium, Trichoderma, Humicola, Thermomyces*, and *Bacillus*. Commercially available preparations comprising xylanase include SHEARZYME®, BIOFEED WHEAT®, BIO-FEED Plus®L, ULTRAFLO®, VISCOZYME®, PENTOPAN MONO®BG, and PULPZYME®HC (Novozymes A/S), and LAMINEX® and SPEZYME®CP (Genencor Int.) An example of a hemicellulase suitable for use in the present invention includes VISCOZYME® (available from Novozymes A/S, Denmark). Hemicellulase loadings vary with coarse fraction hemicellulose content and is generally about 5, 10, 20 or 30, and ranges thereof, mg enzyme protein per gram of hemicellulose in the coarse fraction. The C5 sugar content of the coarse fraction hydrolyzate represents a yield of at least about 25%, about 30%, about 35%, about 40%, about 45% or at least about 50% based on the hemicellulose content of the coarse fraction.

An α-amylase may be added to liquefy free starch that was formerly entrapped within the cellulose, hemicellulose and/or lignocellulosic matrices and/or to liquefy starch that was otherwise not hydrolyzed in the primary liquefaction step. α-amylase loading varies with the starch content in the hydrolyzed coarse fraction and is typically 0.05, 0.1, 0.15, 0.2, and ranges thereof, wt. % of coarse fraction solids. A β-amylase may be added to convert liquefied starch to C6 sugars. Pullulanases are a class of glucanases that catalyze the hydrolysis of amylopectin at the 1→6 bond, thereby yielding oligomers of D-glucose. A commercially available pullulanase is Promozyme® D2, available from Novozyme Corporation.

Also useful are multienzyme complexes containing multiple carbohydrases, such as Viscozyme® L, available from Novozyme Corporation, which contains arabanase, cellulase, β-glycanase, hemicellulase, and xylanase.

Proteases may be added to hydrolyze peptide bonds that link amino acids together in polypeptide chains to thereby form short chain polypeptides. In general, a portion of the energy crop starch (particularly in the endosperm component) is in the form of fine starch granule encased in a protein matrix. Proteases are useful for hydrolyzing the peptide bonds and releasing the entrapped starch granules. Moreover, proteases enhance the solubility of proteins, oligopeptides, and amino acids in the mash. Without being bound by a particular theory, it is thought that hydrolysis of the proteins into peptides and amino acids enhances the nutritional value of the DDG and/or DDGS prepared from still bottoms after ethanol recovery, since peptides and amino acids are relatively more soluble than proteins and thus may be more bioavailable in the DDG and/or DDGS. Further, short chain polypeptides can be used by yeast for biological activities and thereby increase the fermentation rate by about 5% to about 10%. Generally any of the classes of proteases are applicable, e.g., acid, base, or neutral, and proteases are commercially available from, for example, Novozymes, Genencor and Solvay. Examples include, for instance, GC106 (available Genencor International), AFP 2000 (available from Solvay Enzymes, Inc.), FermGen™ (which is an alkaline protease available from Genencor International), and Alcalase® (which is an acid protease available from Novozymes Corporation). The amount of all acid protease is typically in the range of from about 0.01 to about 10 SAPU per gram of starch, from about 0.05 to about 5 SAPU per gram of starch, or even from about 0.1 to about 1 SAPU per gram of starch. As used herein, "SAPU" refers a spectrophotometric acid protease unit, wherein 1 SAPU is the amount of protease enzyme activity that liberates one micromole of tyrosine per minute from a casein substrate under conditions of the assay.

In some aspects of the present invention, coarse and fine fractions can be generated from a saccharified mash prepared in a no cook process. In this aspect, an aqueous mashing mixture is formed, preferably including backset, as described above. The aqueous mashing mixture is not treated at a temperature at which starch is converted to α-starch or gelatinized. The temperature at which the viscosity increase begins differs depending upon the raw material and its concentration, and typically is in the range of from about 55° C. to about 95° C. Instead, an enzyme source comprising a saccharification enzyme, such as glucoamylase, is added to the aqueous mashing mixture and the mixture is processed below the gelatinization temperature so that saccharification occurs directly from the raw native insoluble starch to soluble glucose while bypassing conventional starch gelatinization conditions. The no-cook saccharification mixture thus produced may be fractionated to form (i) a coarse fraction comprising greater than 50% by weight of coarse insoluble particles comprising fiber and greater than 50% by weight of the insoluble starch contained in the no-cook saccharification mixture and (ii) a fine fraction comprising greater than 50% by weight of the fine insoluble particles and greater than about 50% by weight of the soluble glucose contained in the no-cook saccharifcation mixture. The coarse fraction may then be hydrolyzed by contact with an enzyme source comprising a cellulase, and optionally at least one hemicellulase, to form fermentable C5 and C6 sugars. In one no-cook process aspect, the hydrolyzed coarse fraction and fine fraction can be combined and further contacted with an enzyme source comprising an α-amylase enzyme, a glucoamylase enzyme, a protease, and combinations thereof to form a soluble sugar composition that can optionally be combined with a fermentation organism source for the generation of ethanol. In another no-cook process aspect, the coarse fraction hydrolyzate can prepared from an enzyme source comprising a cellulase and an α-amylase enzyme, a glucoamylase enzyme, a protease, and combinations thereof to form a soluble sugar composition that is then combined with the no-cook process fine fraction to form a no-cook soluble sugar composition that can optionally be combined with a fermentation organism source for the generation of ethanol. In another no-cook process aspect, the coarse fraction hydrolyzate can prepared from an enzyme source comprising a cellulase and an α-amylase enzyme. The coarse fraction hydrolyzate can then be combined with the fine fraction and subjected to saccharification by contact with an enzyme source comprising a glucoamylase to form a soluble C5 and C6 sugar solution that can optionally be combined with a fermentation organism source for the generation of ethanol. In one option of this aspect, the hydrolyzed no-cook coarse fraction the fine fraction can be process to ethanol by a SSF process.

It is believed that processing a coarse fraction to a coarse fraction hydrolyzate as presently disclosed provides for significant processing improvements. For instance, as compared to prior art liquefied mashes, the fiber (cellulose) concentration in the coarse fraction of the present invention is about two to about five times greater than the fiber concentration in prior art liquefied mashes. This enables relatively high loading of cellulase enzyme, on both total volume and ratio to cellulose bases, to be employed. Thus, in accordance with the present invention, a high loading of enzyme to cellulose is economically practical. In comparison, for a given ratio of cellulase to cellulose, in prior art processes, the cellulose enzyme would be significantly diluted if utilized in prior art low fiber concentration unfractionated, whole fiber, liquefied mashes resulting in accelerated and higher loss of enzyme activity with time. Further, efficient mixing and long residence time are required for effective cellulase activity. Separation of cellulose as a coarse fraction from a liquefaction mixture de-couples complex carbohydrate hydrolysis from the overall process and allows for an increased time for cellulase activity as compared to processing the cellulose contained in an unfractionated liquefied mash. Yet further, some energy crop components that interfere with cellulase activity, such as oil and phenols (e.g., methoxy phenol from lignin), preferentially partition to the fine fraction thereby improving cellulose hydrolysis as compared to a liquefaction mixture that is not fractionated. Yet further, separation of the coarse fraction from the fine fraction de-couples coarse fraction processing from the fine fraction processing thereby (i) allowing for a parallel processing scheme that provides for cycle time and related processing improvements, such as enabling for tailored blends of fine fraction and coarse fraction hydrolyzate, (ii) allowing for selective application of a variety of enzymes to fiber, starch and/or protein components in order to maximize the amount of fermentable sugar derivable from the energy feedstock, (iii) allowing for batch or continuous coarse fraction processing in combination with batch or continuous fine fraction processing, and (iv) providing a flexible process that can be used to maximize processing efficiency from a wide variety of energy crop feedstocks having varying starch and fiber compositions. It is believed that the hexose sugar yield is at least about 30%, about 40%, about 50% or about 60% based on the polysaccharide content of the coarse fraction.

Combined Liquefaction Admixture

A combined liquefaction admixture is formed by admixing at least a portion of the coarse fraction hydrolyzate and at least a portion of the fine fraction. In general, the combined liquefaction admixture comprises a weight ratio of the coarse fraction hydrolyzate to the fine fraction of about 1:99, about 5:95, about 10:90, about 15:85, about 20:80, about 25:75, about 30:70, about 35:65, about 40:60, about 45:55, about 50:50, and ranges thereof, for instance, from about 1:99 to about 50:50, from about 5:95 to 50:50, from about 10:90 to about 50:50, from about 15:85 to about 50:50 or from about 20:80 to about 50:50. The coarse fraction hydrolyzate and fine fraction may be admixed by a variety of means known in the art including, without limitation, a static mixer, a dynamic mixer, or a mixing vessel.

The combined liquefaction admixture is adjusted to a pH of about 3.5, about 4, about 4.5 or about 5, and ranges thereof, such as from about 4 to about 5 or from about 4.2 to about 4.8, such as about 4.5, and to a temperature of from about 25° C. to about 40° C. Those conditions are favorable for saccharification and fermentation. In some aspects, the coarse fraction hydrolyzate and/or fine fraction are cooled to from about 25° C. to about 40° C., prior to admixing, during admixing, or after admixing. In some other aspects, the pH of the coarse fraction hydrolyzate and/or fine fraction is adjusted prior to admixing, during admixing, or after admixing. In one aspect, admixing, pH and temperature adjustment are done in a mixing vessel.

Saccharification and Fermentation

In a saccharification step, the oligosaccharides resulting from the liquefaction and coarse fraction hydrolysis process may be converted to smaller polysaccharides and eventually to monosaccharides, such as glucose, by hydrolysis. The adjusted combined liquefaction admixture is contacted with glucoamylase (β-amylase) enzyme to generate fermentable glucose by cleavage of the last α(1→4) glycosidic linkages at the nonreducing end of amylose and amylopectin and by cleavage of α(1→6) glycosidic linkages. Generally, from about 1 to about 6 glucoamylase units (GAU) per gram of dry solids in the combined liquefied admixture are added to the combined liquefied admixture. Preferred glucoamylases are of fungal or bacterial origin and are suitably selected from *Aspergillus glucoamylases*, (e.g., *A. niger* G1, *A. niger* G2, *A. awamori, A. oryzae*, or variants or fragments thereof). Other *Aspergillus* variants include variants to enhance the thermal stability. Still other *glucoamylases* include *Talaromyces glucoamylases* such as those derived from *Talaromyces emersonii, Talaromyces leycettanus, Talaromyces duponti* and *Talaromyces thermophilus*. Bacterial *glucoamylases* contemplated include *glucoamylases* from the genus *Clostridium*, in particular *C. thermoamylolyticum*, and *C. thermohydrosulfuricum*. Commercially available compositions comprising glucoamylase include: AMG 200L, AMG 300 L, AMG E, SAN® SUPER, SAN® EXTRA L, SPIRIZYME® PLUS, SPIRIZYME® FUEL, SPIRIZYME® FG and SPIRIZYME® E (all available from Novozymes); OPTIDEX® 300 and DISTILLASE® L-400 (available from Genencor Int.); and G-ZYME™ G900, G-ZYME™ 480 Ethanol and G990 ZR (all available from Genencor Int.). Glucoamylases may be added in an amount of from about 0.02 to about 20 glucoamylase units per gram DS ("AGU/g"), from about 0.1 to about 10 AGU/g DS, or even from about 1 to about 5 AGU/g DS.

The cellulase enzyme from the coarse fraction hydrolysis step continues to hydrolyze cellulose fibers in the combined liquefaction mixture at the lower pH and temperature conditions required for saccharification and fermentation, resulting in further glucose and ethanol yield per unit weight of energy crop. Optionally, a protease enzyme, as explained above, may be added to the combined liquefaction mixture.

In a fermentation step the saccharified and adjusted combined liquefaction admixture is inoculated with an ethanol fermentation organism source comprising at least one species of an organism, such as yeast, capable of converting hexose sugars (e.g., glucose) to ethanol. In one aspect, the glucoamylase enzyme is added prior to the yeast in a pre-saccharification step, lasting for about 15 minutes to about 2 hours, for example from about 30 minutes to about 60 minutes. In another aspect, yeast and glucoamylase are added to the fermentation medium at a closely spaced time interval, or simultaneously. In either aspect, when glucoamylase enzyme and yeast are both present, fermentation and saccharification predominantly occurs simultaneously.

In some aspects of the present invention, the ethanol fermentation organism source further comprises one or more pentose sugar (e.g., xylose) fermenting organisms. In yet other aspects, the ethanol fermentation organism source comprises one or more species of organisms capable of metabolizing both hexose and pentose sugars to ethanol. In still other aspects, the ethanol fermentation organism source further comprises one or more species of cellulolytic organisms capable of converting cellulose to ethanol. In yet other aspects, the ethanol fermentation organism source further comprises one or more species of hemicellulolytic organisms capable of converting hemicellulose to ethanol. Combinations of an organism capable of converting hexose sugars to ethanol, an organism capable of converting pentose sugars to ethanol, an organism capable of converting both hexose and pentose sugars to ethanol, a cellulolytic organism and a hemicellulolytic organism are within the scope of the present invention. Combinations of an organism capable of converting both hexose and pentose sugars to ethanol, a cellulolytic organism and a hemicellulolytic organism are within the scope of the present invention. Such organisms are known in the art and are suitable selected from yeast, bacteria, fungi and transgenic species thereof.

The saccharification and fermentation steps may be performed in accordance with methods known in the art. For instance, in some aspects, saccharification of the liquefied medium can be done to some extent prior to fermentation. In these aspects, a portion or even all of the glucoamylase is added to the liquefied medium prior to the addition of ethanol fermentation organisms. Glucoamylase addition may occur batchwise or continuously. Addition of the glucoamylase to the liquefied medium prior to addition of the fermentation organism thereby forms a saccharification medium. The fermentation organism is then added to the saccharification medium to form ethanol. In some other aspects, the adjusted combined liquefaction admixture may be subjected to simultaneous saccharification and fermentation wherein glucoamylase enzyme and the fermentation organism are added simultaneously or sequentially within a closely spaced time interval to a SSF reactor. SSF is generally conducted in accordance with conventional methods known in the art including, for example, as described in Dowe et al., "SSF Experimental Protocols-Lignocellulosic Biomass Hydrolysis And Fermentation", National Renewable Energy Laboratory, 2001, 18 pages, the entire contents of which are incorporated herein by reference for all relevant purposes. The configuration of the SSF reactor is not narrowly critical and may be readily selected by one skilled in the art. Preferably, the SSF reactors are suitable for batch or continuous operation (e.g., an individual or a series of continuous stirred-tank reactors).

In some aspects, at least a portion of the glucoamylase is mixed with at least a portion the combined liquefaction mixture within the concentration ranges above prior to mixing with the fermentation organism. In batch propagation or fermentation processes, described in detail below, such prior mixing is believed to expose the fermentation organism to a consistent initial concentration of simple sugars, neither starving the fermentation organism with a low initial concentration nor inhibiting the fermentation organism with a high initial concentration. In some other aspects, substantially all the of glucoamylase and combined liquefaction mixture are combined within the concentration ranges above prior to the addition of fermentation organism.

To enhance the efficiency of saccharification and ethanol fermentation and increase the ethanol yield, additional nutrients may be added to enhance yeast activity. Such nutrient includes, without limitation, free-amino-nitrogen (FAN), oxygen, phosphate, sulfate, magnesium, zinc, calcium, and vitamins such as inositol, pantothenic acid, and biotin. Typical sources of FAN include urea, ammonium sulfate, ammonia, amino acids, and α-amino nitrogen groups of peptides and proteins. Added FAN content is preferably from about 1.2 to about 6 mg N/g starch, for example 1.2, 2.4, 3.6, 4.8 or 6 mg N/g starch. In the case of urea, it is preferred to add from about 2.4 to about 12 mg urea per gram of starch, for example, 2.4, 4.8, 7.2, 9.6 or 12 mg urea per gram of starch. Yeast foods that supply, for example, vitamins (such a B vitamins and biotin), minerals (such as from salts of magnesium and zinc) and micronutrients and nutrients can be added to the fermentation medium. Yeast foods can include autolyzed yeast and plant extracts and are typically added to a concentration of from about 0.01 to about 1 g/L, for example from about 0.05 to about 0.5 g/L. Bactericides can also optionally be added to the fermentation medium. Examples of typical bactericides include virginiamycin, nisin, erythromycin, oleandomycin, flavomycin, and penicillin G. In the case of virginiamycin, a concentration of from about 1 ppm to about 10 ppm is preferred.

A fermentation pH of about 3.5 to about 6, from about 3.5 to about 5 or from about 4 to about 4.5 is preferred. If pH adjustment is required, mineral acids such as sulfuric acid, hydrochloric acid or nitric acid may be used or bases such as ammonia (ammonium hydroxide) or sodium hydroxide may be used. A fermentation temperature of from about 30° C. to about 36° C., from about 31° C. to about 35° C. or from about 32° C. to about 34° C. is preferred. For yeast-based batch fermentation, a propagation mixture comprising adapted yeast that has been generated from a fermentation mixture comprising the saccharified and adjusted combined liquefaction admixture may optionally be initially charged to a fermentation vessel. Typically, such initial charge comprises about 2% to about 5% of the initial primary fermentation mixture volume.

At the end of saccharification and fermentation, the alcohol content in the beer may range from about 10% to about 15% by weight as is basis, typically from 12% to about 15% by weight as is basis, as measured by any suitable means, such as by high performance liquid chromatograph (HPLC), and corrected for suspended solids in the beer.

Hexose sugar fermenting organisms within the scope of the present invention include yeasts. Any of a variety of yeasts can be employed in the present process. Typical yeasts include any of a variety of commercially available yeasts, such as commercial strains of *Saccharomyces cerevisiae*. Suitable commercially available strains include ETHANOL RED (available from Red Star/Lesaffre, USA); BioFenn HP and XR (available from North American Bioproducts); FALI (available from Fleischmann's Yeast); SUPERSTART (available from Lallemand); GERT STRAND (available from Gert StrandAB, Sweden); FERMIOL (available from DSM Specialties); and Thennosac (available fromAlltech). In some aspects, the hexose fermenting organism is a recombinant yeast having at least one transgene expressing an enzyme useful for converting mono- and/or -oligo-saccharides to ethanol.

In some aspects of the present invention, the yeast may be adapted to the primary fermentation mixture prior to fermentation to ethanol by propagating yeast in at least a portion of the liquefied medium. Propagation is typically performed by forming a propagation mixture comprising yeast, liquefied medium or enzymatic hydrolysate, glucoamylase, and additional nutrients. The propagation mixture may then be aerated. In aerobic conditions, the yeast preferentially converts glucose and other hexose sugars to form more yeast. It is believed that such yeast progeny are more efficient at converting hexose sugars to ethanol in a saccharification and ethanol fermentation process performed on the primary fermentation mixture. For batch propagation, propagation is performed for about 15 hours once all ingredients are added to the propagation vessel, after which time the contents of the propagation vessel are preferably transferred to a fermentation vessel. For the reasons stated above, a batch propagation process preferably comprises mixing glucoamylase with at least a portion of the liquefied medium or enzymatic hydrolysate within the glucoamylase concentration ranges described above prior to mixing with yeast to form the propagation mixture.

Pentose sugar (e.g., xylose) fermenting organisms within the scope of the present invention include yeasts. Such yeasts include *Pachysolen tannophilus, Pichia stipites, Candida diddensii, Candida utilis, Candida tropicalis, Candida subtropicalis, Saccharomyces diastaticus, Saccharomycopsis*

*fibuligera* and *Torula candida*. In some aspects, the pentose fermenting organism is a recombinant yeast having at least one transgene expressing an enzyme useful for converting mono- and/or -oligo-saccharides to ethanol. For instance, the genome of *P. stipites* may be incorporated into *S. cerevisiae* by a gene shuffling method to produce a hybrid yeast capable of producing bioethanol from xylose while retaining the ability to survive in high concentrations of ethanol.

Organisms capable of fermenting both hexose and pentose sugars include transgenic yeast strains. Typically, such organisms are strains of *S. cerevisiae* having transgenes encoding for one or more enzymes capable of converting pentose sugars to ethanol.

In some aspects of the present invention, the fermentation organism source comprises at least one species of cellulolytic organism capable of breaking down non-hydrolyzed cellulose present in the adjusted combined liquefaction admixture to fermentable sugars such as monosaccharides and polysaccharides. In some other aspects, the cellulolytic organism comprises ethanol-producing pathway genes allowing for the synthesis of ethanol from fermentable sugars. Such cellulolytic organism are known and include *Escherichia coli*, *Zymomonas mobilis*, *Bacillus stearothermophilus*, *Saccharomyces cerevisiae*, *Clostridia thermocellum*, *Thermoanaerobacterium saccharolyticum*, *Pichia stipites* and *Pachysolen tannophilus*. Also within the scope of the present invention are cellulolytic bacteria having one or more transgenes encoding for the ethanol-producing pathway.

In some aspects of the present invention the fermentation organism source comprises at least one species of cellulolytic organism capable of breaking down non-hydrolyzed hemicellulose present in the adjusted combined liquefaction admixture to fermentable sugars such as monosaccharides and polysaccharides.

In any of the various hexose and/or pentose fermentation aspects of the present invention, the liquefied medium or enzymatic hydrolysate is typically inoculated with yeast to a concentration of from about $1 \times 10^7$ cells/mL and about $1 \times 10^{11}$ cells/mL or from about $1 \times 10^8$ cells/mL and about $1 \times 10^{10}$ cells/mL. Generally, yeast inoculum introduced into the fermentation vessel comprises the yeast dispersed throughout an aqueous medium. Typically, the yeast content of the yeast inoculum is from about 0.1 to about 5 wt. % and, more typically, from about 1 to about 2.5 wt. %. The relative proportions of yeast inoculum and cellulose hydrolyzate introduced into the fermentation vessel depend on a variety of factors including, for example, the composition of each stream. Generally, however, the mass ratio of yeast inoculum to hydrolyzate introduced into the fermentation vessel is from about 0.01:1 to about 0.25:1, or from about 0.02:1 to about 0.1:1.

Saccharification and fermentation are complete after a period of operation of less than about 168 hours, about 144 hours, about 120 hours, about 96 hours, about 84 hours, about 72 hours or less than about 60 hours. Generally, the fermentate (also termed "beer") is a mixture of water, ethanol, unconverted hexose and pentose sugars, fibers (e.g., cellulose, hemicellulose and lignocellulose), lignin and ash. The overall composition of the fermentate generally varies depending on, for example, the composition of the enzymatic hydrolyzate, the ethanol fermentation organism source, and the relative proportions introduced into the saccharifaction and fermentation vessels or SSF vessel. In some aspects of the present invention, the process of the present invention provides for an ethanol yield of 85%, 86%, 87%, 88%, 89%, 90%, 91%, 92%, 93%, 94% or 95%, and ranges thereof, based on the total starch content of the energy crop. For #2 yellow corn, in some aspects, the present invention provides for a yield of at least 2.85, 2.9, 2.95, 3, 3.05, or 3.1 gallons of ethanol per bushel (56 pounds), or alternatively expressed as at least 0.424, 0.432, 0.439, 0.447, 0.454 or 0.461 liters per kilogram.

Ethanol Recovery

After the fermentation is complete, the beer is fed to a reboiler where ethanol and volatile impurities (e.g., fusel oil (predominantly comprising amyl alcohol)) are separated by vaporization in a distillation column leaving reboiler bottoms containing dissolved solids. Generally, conventional distillation apparatuses known in the art are suitable for use in accordance with the present invention. Conventional apparatuses are described, for instance, in Distillation Technology, GEA Wiegand GmbH, publication P06E 022009 (2013) and Bioethanol Technology, GEA Wiegand GmbH, publication P11E (2013), the entire contents of which are incorporated herein by reference for all relevant purposes. Examples of suitable distillation columns include columns having dual flow and cross flow trays, such as dual flow sieve trays or cross-flow valve trays. In some aspects, cross flow valve trays are used because of the higher turn down ratio and higher they provide. Suitable valve trays include, for example, NORPRO PROVALVE trays. Ethanol is condensed and purified in the distillation column. The liquid ethanol exits the top of the distillation column at about 95% purity from where it passes through a molecular sieve dehydration column which removes at least about 75%, about 80%, about 85%, about 90%, about 95% or even at least about 99% of the remaining residual water.

The liquid reboiler bottoms (i.e., still bottoms) are fed to a centrifuge in order to separate the insoluble solids (termed "un-dried distillers grains") from the liquid centrifugate (termed "thin stillage"). The un-dried distillers grains may be optionally dried to form dried distillers grains ("DDG"). The thin stillage may be fed to one or more evaporators in an evaporation step in order to remove moisture leaving a thick syrup typically containing from about 30 wt. % to about 40 wt. % soluble (dissolved) solids from the fermentation. In one aspect, the concentrated syrup can be mixed with the un-dried distillers grains to from un-dried distillers grains plus solubles ("DDGS"). The un-dried DDGS can be optionally dried to form dried DDGS. Dried DDG and DDGS are typically used as ruminant (cattle) feed. In some aspects, at least a portion of the dried or un-dried DDG and/or DDGS may be recycled to the aqueous mashing mixture or liquefied mash for recovery of fermentable sugars. In some other aspects, at least a portion of the still bottoms and/or thin stillage may be recycled to the aqueous mashing mixture or liquefied mash for recovery of fermentable sugars. In still other aspects, the thin stillage may be clarified prior to recycle by conventional means known in the art such as by a decanter centrifuge or by a filter press.

DDG and DDGS prepared by the process of the present invention is characterized as having low fiber content and high oil and protein content as compared to DDG and DDGS prepared from conventional starch to ethanol processes. DDG and DDGS of the present invention may be characterized as having, on weight percent dry basis: a protein content of about 29%, 30%, 31%, 32% or 33%, and ranges thereof, such as from about 29% to 33%, 30% to 33% or 31% to 33%; about 7%, 8%, 9%, 10%, 11% or 12% weight total oil; about 2%, 3%, 4%, 5% or 6% acid detergent fiber ("ADF"); about 5%, 10%, 15%, neutral detergent fiber ("NDF"); about 2%, 3%, 4%, 5%, 6% or 7% ash; and about 2%, 4%, or 6% starch.

EXAMPLES

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Example 1

A liquefied mash was prepared from a mixture of water, dry milled corn and alpha-amylase. The pH of the liquefied mash was adjusted to between 4.5 and 5.0 and fractionated through a mesh having a mesh size of from 0.5 mm to 2 mm to form a fine fraction (undersize) and coarse fraction (oversize). As shown in Table 1 below, the coarse fraction was hydrolyzed with three different cellulase loadings of 0.036, 0.18 and 0.36 wt. % Cellic® CTec3 (Novozymes) cellulase based on dry solid content of the coarse fraction, wherein those trials are designated as trial numbers 2, 3 and 4, respectively. Trial 1 was a comparative trial wherein no cellulase was added to the coarse fraction. Following a cellulase hydrolysis period, disclosed in Table 1, the hydrolyzed coarse fraction of each of trials 2-4 and the non-hydrolyzed coarse fraction of trial 1 were each combined with their respective fine fraction and inoculated with the same loading of glucoamylase and yeast. SSF was conducted for the indicated period of time wherein fermentation was deemed complete. Total ethanol yield was then determined.

Table 1 shows the improvement in ethanol yield from corn mash when cellulase is added to the coarse fraction. The ethanol yield improvement over the control (no cellulase added) ranges from 1.9% to 3.4%.

TABLE 1

Improvement in ethanol yield with hydrolysis of fiber in the coarse fraction using Novozymes Celic CTec3 enzyme.

| No | Cellulase loading, wt % dry solids | Cellulase Hydrolysis time, hr | Hydrolyis time after addition of glucoamylase, hr | Increase in ethanol yield, % |
|---|---|---|---|---|
| 1 | 0 (control) | 0 | 63 | N/A |
| 2 | 0.036 | 24 | 70 | 2.7 |
| 3 | 0.18 | 3.3 | 63 | 1.9 |
| 4 | 0.36 | 8 | 63 | 3.4 |

What is claimed is:

1. A process for preparing a composition comprising glucose, the process comprising:
   (1) forming a mashing mixture comprising a milled energy crop, water and an alpha-amylase enzyme;
   (2) forming a liquefied mash from the mashing mixture, the liquefied mash comprising (i) coarse insoluble particles comprising cellulose, (ii) non-liquefied starch particles, (iii) fine insoluble particles and (iv) liquefied starch;
   (3) forming an adjusted liquefied mash by the liquefied mash to a pH suitable for hydrolysis of cellulose by cellulase enzyme;
   (4) fractionating the adjusted liquefied mash to form (i) a coarse fraction comprising greater than 50% by weight of coarse insoluble particles contained in the adjusted liquefied mash and greater than 50% by weight of the non-liquefied starch contained in the adjusted liquefied mash and (ii) a fine fraction comprising greater than 50% by weight of the fine insoluble particles contained in the adjusted liquefied mash and greater than about 50% by weight of the liquefied starch contained in the adjusted liquefied mash;
   (5) admixing at least a portion of the coarse fraction with at least one cellulase enzyme and liquefying the admixture to form a coarse fraction hydrolyzate; and
   (6) (i) admixing at least a portion of the coarse fraction hydrolyzate with at least a portion of the fine fraction to form a combined liquefied admixture, (ii) adding a glucoamylase enzyme to the combined liquefied admixture, and (iii) saccharifying the combined liquefied admixture to form the composition comprising glucose.

2. The process of claim 1 wherein a plurality of coarse insoluble particles has a particle size in excess of about 300 microns and a plurality of fine insoluble particles has a particle size of less than about 300 microns.

3. The process of claim 1 further comprising adding at least one species of ethanol fermentation organism to the composition comprising glucose to form a fermentation mixture, and fermenting the fermentation mixture to form beer comprising ethanol.

4. The process of claim 1 wherein the mashing mixture has a solids content of from about 15% to about 40% on a dry matter weight basis.

5. The process of claim 1 wherein the adjusted liquefied mash is fractionated by (i) contact with a mesh having a mesh size of from about 0.5 mm to about 2 mm or (ii) by contact with a perforated screen having a hole diameter of from about 0.5 mm to about 2 mm, wherein the fine fraction is an undersize fraction that passes through the mesh or perforation and the coarse fraction is an oversize fraction.

6. The process of claim 1 wherein the coarse fraction comprises from about 55% to about 90% by weight of the coarse insoluble particles contained in the adjusted liquefied mash and from about 55% to about 90% of the non-liquefied starch contained in the adjusted liquefied mash.

7. The process of claim 1 wherein the fine fraction comprises from about 55% to about 90% by weight of the fine insoluble particles contained in the adjusted liquefied mash and from about 55% to about 90% of the liquefied starch contained in the adjusted liquefied mash.

8. The process of claim 1 wherein the weight ratio of the coarse fraction to the fine fraction is from about 1:6 to about 1:1.2.

9. The process of claim 1 further comprising reducing the particle size of the coarse fraction particles by thermal or mechanical means to generate a reduced particle size coarse fraction wherein a plurality of the coarse particles have an average particle size of from about 100 microns to about 250 microns, and wherein a plurality of the particles of the non-liquefied starch have an average particle size of from about 100 microns to about 250 microns.

10. The process of claim 1 wherein the total cellulase loading is from about 5 to about 50 filter paper units (FPU) per gram of cellulose.

11. The process of claim 1 wherein the total cellulase loading is from about 0.25 to about 10 filter paper units (FPU) per gram of coarse fraction.

12. The process of claim 1 wherein the coarse fraction is liquefied in at least one liquefaction reactor comprising at least one mixing section and at least one plug flow section.

13. The process of claim 1 wherein the coarse insoluble particles further comprise hemicellulose and the coarse fraction comprises from about 10% to about 40% by weight hemicellulose, the process further comprising admixing the coarse fraction with a hemicellulase enzyme.

14. The process of claim 13 wherein total hemicellulase loading is from about 5 to about 30 mg enzyme protein per gram of hemicellulose.

15. The process of claim 13 wherein the pentose sugar content of the coarse fraction represents a yield of at least about 25% based on the hemicellulose content of the coarse fraction.

16. The process of claim 1 wherein the weight ratio of the coarse fraction hydrolyzate to the fine fraction in the combined liquefied admixture is from about 1:99 to about 50:50.

17. The process of claim 3 wherein the ethanol fermentation organism comprises a hexose fermenting yeast.

18. The process of claim 3 wherein the ethanol fermentation organism further comprises a pentose fermenting organism.

19. The process of claim 3 wherein the ethanol fermentation organism comprises an organism capable of fermenting both hexose and pentose sugars.

20. The process of claim 3 wherein the saccharification and fermentation are performed simultaneously.

21. The process of claim 3 wherein from about 92% to about 94% percent of the available starch in the energy crop weight is converted to ethanol.

22. The process of claim 3 wherein from about 20% to about 30% of the cellulose by weight is converted to ethanol.

23. The process of claim 3 further comprising (i) distilling the beer to form ethanol and whole stilling and (ii) recovering distillers grain from the whole stillage, wherein the distillers grain comprises from 29% to 31% protein on a dry basis.

\* \* \* \* \*